(12) United States Patent
Prinz et al.

(10) Patent No.: US 7,119,237 B2
(45) Date of Patent: Oct. 10, 2006

(54) PROCESS AND CATALYST FOR PREPARING ALCOHOLS

(75) Inventors: Thomas Prinz, Leverkusen (DE); Jürgen Kintrup, Leverkusen (DE); Andreas Schulze Tilling, League City, TX (US); Jörg-Dietrich Jentsch, Krefeld (DE); Gerald John, Düsseldorf (DE); Hans-Jürgen Grob, Duisburg (DE); Guido Giffels, Bonn (DE)

(73) Assignee: Bayer Aktiengesellschaft, Leverkusen (DE)

( * ) Notice: Subject to any disclaimer, the term of this patent is extended or adjusted under 35 U.S.C. 154(b) by 110 days.

(21) Appl. No.: 10/368,767

(22) Filed: Feb. 19, 2003

(65) Prior Publication Data

US 2003/0187309 A1 Oct. 2, 2003

(30) Foreign Application Priority Data

Feb. 22, 2002 (DE) .................. 102 07 443

(51) Int. Cl.
*B01J 23/02* (2006.01)
*B01J 23/06* (2006.01)
*C07C 27/04* (2006.01)
*C07C 29/149* (2006.01)

(52) U.S. Cl. .............. 568/885; 502/342; 502/343; 502/346; 502/355; 502/415; 502/439

(58) Field of Classification Search ............. 502/342, 502/343, 346, 355, 415, 439; 568/799, 864, 568/881, 885
See application file for complete search history.

(56) References Cited

U.S. PATENT DOCUMENTS

| | | | | |
|---|---|---|---|---|
| 4,305,842 A | | 12/1981 | Asakawa et al. .......... 252/432 |
| 4,393,251 A | | 7/1983 | Broecker et al. .......... 568/811 |
| 4,535,071 A | * | 8/1985 | Schneider et al. ......... 502/342 |
| 4,977,123 A | * | 12/1990 | Flytzani-Stephanopoulos et al. ................ 502/84 |
| 5,019,547 A | | 5/1991 | Chaumette et al. ......... 502/342 |
| 5,134,108 A | * | 7/1992 | Thakur et al. ............. 502/318 |
| 5,155,086 A | | 10/1992 | Thakur et al. ............. 502/342 |
| 5,334,779 A | | 8/1994 | Kuo .......................... 568/864 |
| 5,343,005 A | | 8/1994 | Salzmann ................ 200/61.89 |
| 5,345,005 A | | 9/1994 | Thakur et al. ............. 568/885 |
| 5,395,990 A | * | 3/1995 | Scarlett ..................... 568/864 |
| 5,453,412 A | | 9/1995 | Deckers et al. ............ 502/342 |
| 5,696,303 A | | 12/1997 | Darsow et al. ............ 568/864 |
| 5,935,898 A | * | 8/1999 | Trubenbach et al. ....... 502/150 |
| 5,985,790 A | * | 11/1999 | Moskovitz et al. ......... 502/415 |
| 5,990,373 A | * | 11/1999 | Klabunde ................... 588/313 |
| 6,054,627 A | * | 4/2000 | Thakur et al. ............. 568/799 |
| 6,124,234 A | | 9/2000 | Fetzer et al. ............... 502/326 |
| 6,153,162 A | * | 11/2000 | Fetzer et al. ............. 423/239.1 |
| 6,218,335 B1 | * | 4/2001 | Okada et al. .............. 502/340 |
| 6,383,273 B1 | * | 5/2002 | Kepner et al. .......... 106/15.05 |
| 6,455,464 B1 | | 9/2002 | Chen ......................... 502/346 |
| 6,521,197 B1 | | 2/2003 | Kumberger et al. ..... 423/437.1 |
| 6,576,588 B1 | * | 6/2003 | Ryu et al. .................. 502/331 |

FOREIGN PATENT DOCUMENTS

| | | |
|---|---|---|
| DE | 199 42 895 | 3/2001 |
| DE | 199 42 895 A | 3/2001 |
| EP | 0 424 069 | 10/1990 |
| EP | 0 901 815 A1 | 3/2000 |
| JP | 9-173845 | 7/1997 |
| WO | 82/03854 | 11/1982 |
| WO | WO 02/081416 A2 | 10/2002 |

OTHER PUBLICATIONS

Handbook of Catalysis, VCH Wiley, Weinheim month unavailable, 1997, pp. 1836-1838 "Energy-Related Catalysis".
Studies in surface science and catalysis, 16, Elsevier, Amsterdam, month unavailable, 1983, pp. 735-755, G. Petrini et al, "Preparation and Characterization of Very Active Cu/ZnO and Cu/ZnO/Al$_2$O$_3$ LTS Catalysts Using a Single Phase Cu-Zn Precursor Compound".

* cited by examiner

*Primary Examiner*—Cam N. Nguyen
(74) *Attorney, Agent, or Firm*—Nicanor Köhncke; Jennifer R. Seng

(57) ABSTRACT

Alcohols prepared by reacting carboxylic acids and/or carboxylic esters with hydrogen in the presence of a special catalyst.

18 Claims, No Drawings

PROCESS AND CATALYST FOR PREPARING ALCOHOLS

BACKGROUND OF THE INVENTION

1. Field of the Invention

The present invention relates to a process for preparing alcohols by reacting carboxylic acids and/or carboxylic esters with hydrogen in the presence of a special catalyst, and to such catalysts.

2. Brief Description of the Prior Art

The hydrogenation of carboxylic acids and carboxylic esters in the presence of catalysts based on copper chromite (Adkins catalyst) has been known for some time. However, the use of chromium-containing catalysts is undesirable for reasons of the associated risks to the environment. Efforts have therefore been made to replace these chromium-containing catalysts by more environmentally friendly chromium-free catalysts.

For instance, WO 82/03854 A1 discloses a process for hydrogenating carboxylic esters in the presence of a catalyst which comprises a reduced mixture of copper oxide and zinc oxide.

EP-A 0 721 928 describes a process for preparing aliphatic α,ω-diols by hydrogenating carboxylic esters using a catalyst which comprises a reduced mixture of pressed powders of copper oxides, zinc oxides and aluminium oxides, to which iron oxide, nickel oxide or manganese oxide may be added.

U.S. Pat. No. 5,155,086 describes pulverulent hydrogenation catalysts based on copper/zinc/aluminium which contain a majority of oxides of copper and zinc, and relatively small amounts of aluminium oxide, and the pore volume of the pores which have a diameter of 120 to 1000 Å is at least 40% of the total pore volume. In particular the catalysts are suitable for hydrogenating aldehydes, ketones, carboxylic acids and carboxylic esters.

Catalysts based on copper/zinc/aluminium are known from methanol synthesis (U.S. Pat. No. 4,305,842, EP 125 689 A2). In these catalysts, aluminium oxide and zinc oxide have the function of a support material for copper. Such catalysts are prepared, for example, by coprecipitating the components and converting to active catalysts by calcining and reducing (Knözinger, Ertl, Weitkamp, Handbook of Catalysis, VCH Wiley, Weinheim 1997, 1836).

Hydrogenation catalysts based on copper/zinc/aluminium are also known in which colloidal $TiO_2$ or $Al(OH)_3$ have been added to the product of coprecipitating copper and zinc (EP 125 689 A2, Petrini et al., Preparation of catalysts III, Studies in surface science and catalysis, 16, Elsevier, Amsterdam, 1983, 735–755.)

JP J09-173845 describes the preparation of Cu/Zn catalysts which are prepared by saturating γ-aluminium oxides and have an aluminium content of approx. 53%, and the use of such catalysts in the synthesis of dimethyl ether.

WO 99/4974 describes catalysts which are prepared by precipitating Cu and Zn onto $TiO_2$. To prepare the tablets from the pulverulent catalyst, metallic copper powder is added as a tableting assistant in order to achieve a sufficient hardness. DE 19942895 likewise describes the effectiveness of metallic copper or cement as tableting assistants for preparing Cu/Zn/Al catalysts for hydrogenating carboxylic esters. This addition also leads to an increase in the lateral fracture hardness.

WO 97/34694 describes Cu/Al/Zn catalysts having an Al content of greater than 20% which, in the form of extrudates, have a bimodal pore size distribution. These catalysts are very suitable for the hydrogenation of fatty esters.

When used in fixed bed reactors, the existing catalysts are used as shaped bodies which only have limited mechanical stability under the mechanical stresses occurring there. In addition, the hydrogenation activity of these catalysts, particularly in the hydrogenation of esters of polybasic acids with polyhydric alcohols, for example mixtures of oligomeric esters made from adipic acid and hexanediol, is insufficient for the achievement of high space-time yields.

It is therefore an object of the invention to provide a process for preparing alcohols by reacting carboxylic acids and/or carboxylic esters with hydrogen in the presence of a catalyst which is notable for its high mechanical stability under the reaction conditions and a high activity so that relatively high space-time yields are achieved.

SUMMARY OF THE INVENTION

It was found that, surprisingly, catalysts having high mechanical stability and high activity are obtained when compounds of copper and zinc are coprecipitated onto a support material of aluminium oxide powder and the subsequent calcining is carried out in such a way that a bimodal pore size distribution is obtained.

The invention provides a process for preparing alcohols by reacting carboxylic acids and/or carboxylic esters with hydrogen in the presence of a catalyst which, in the non-reduced state, comprises 20 to 80% by weight of CuO, 10 to 80% by weight of ZnO and 1 to 50% by weight of $Al_2O_3$, and has such a pore size distribution that 5 to 15% of the total pore volume is in the pore diameter range of less than 150 Å and 80 to 95% is in the pore diameter range of greater than 250 Å, which is determined by mercury intrusion (mercury porosimetry) in a similar manner to DIN 66133 assuming a cylindrical pore model.

In a preferred embodiment of the invention the catalyst has such a pore size distribution that 5 to 15% of the total pore volume is in the pore diameter range of 37 to 150 Å and 80 to 95% is in the pore diameter range of 250 to 1000000 Å.

In a particularly preferred embodiment of the invention thre catalyst has such a pore size distribution that 5 to 15% of the total pore volume is in the pore diameter range of 37 to 150 Å and 80 to 95% is in the pore diameter range of 250 to 20000 Å.

DETAILED DESCRIPTION OF THE INVENTION

The invention is described more fully hereunder with particular reference to its preferred embodiments. Preference is given to preparing the catalysts to be used according to the invention by precipitating compounds of copper and of zinc onto aluminium oxide powder.

The catalysts to be used according to the invention are notable in particular for their high hydrogenation activity and an exceptional mechanical and chemical stability, in particular, when used in fixed bed reactors employing the liquid phase method.

Preference is given to using catalysts which, in the non-reduced state, comprise 40 to 70% by weight of CuO, 20 to 50% by weight of ZnO and 4 to 10% by weight of $Al_2O_3$.

Particular preference is given to catalysts which, in the non-reduced state, comprise 60 to 70% by weight of CuO, 20 to 27% by weight of ZnO and 4 to 6% by weight of $Al_2O_3$.

The catalysts may additionally comprise compounds of the rare earth metals, alkali metals, alkaline earth metals, Zr, Ti, Co, Mo, V, W, Fe, Co, Ni, Mn and Re in an amount of 0.1 to 3% by weight as promoters.

The total pore volume is preferably in the range from 150 mm$^3$/g to 250 mm$^3$/g.

The specific surface area (determined according to BET, similarly to DIN 66131 by nitrogen adsorption at −196° C.) of the catalysts in the non-reduced state is 5 to 150 m$^2$/g, preferably 5 to 60 m$^2$/g and more preferably 5 to 30 m$^2$/g.

Preference is given to using aluminium oxide powder having a particle size (average particle diameter) of 1 to 100 µm, more preferably 3 to 80 µm, particularly preferably 10 to 50 µm.

The specific surface area of the aluminium oxide powder (determined according to BET) is preferably 100 to 400 m$^2$/g, more preferably 100 to 300 m$^2$/g, and the pore volume is preferably 0.1 to 1.5 ml/g, more preferably 0.4 to 0.8 ml/g.

The sodium content of the aluminium oxide powder is advantageously 0 to 2% by weight, preferably 0.01 to 0.1% by weight.

It is also possible to use pulverulent mixed oxides of aluminium in a similar manner to the aluminium oxide powder, for example those of silicon which have the same physical properties.

The process according to the invention provides alcohols by hydrogenating carboxylic esters and/or carboxylic acids. The feedstocks may be used in technical quality.

Particularly advantageously, dihydric alcohols can be obtained by the process according to the invention by hydrogenating dibasic carboxylic acids and/or their esters with the corresponding alcohols, although a portion of the starting material may consist of higher molecular weight esters.

Particular preference is given to using mixtures of oligomeric esters made from adipic acid and hexanediol as reactants. In this case, the product obtained is 1,6-hexanediol.

Preference is given to working at a temperature of 100 to 350° C., more preferably at 150 to 300° C. and particularly preferably at 200 to 280° C.

The pressure at which the process according to the invention is carried out is preferably 50 to 400 bar, more preferably 100 to 300 bar.

The reaction may, for example, be carried out in a suspension reactor. In this case, the catalyst is used in pulverulent form. The catalyst is preferably a powder having a particle size (average particle diameter) of 20 to 100 µm.

However, the reaction may also be effected, for example, in a fixed bed reactor, advantageously using the catalyst as a shaped body.

It is possible to work in a reactor or a plurality of reactors attached in series.

The process according to the invention may be carried out either without or with the addition of solvents, for example alcohols.

When reacting carboxylic acids with hydrogen, it is advantageous to carry out the hydrogenation in an alcohol as solvent.

Examples of suitable alcohols include methanol, ethanol, propanol, n-propanol, butanediol and hexanediol. Preference is given to using the alcohol as solvent which results from the hydrogenation of the carboxylic acid.

The invention further provides catalysts for the preparation of alcohols by reacting carboxylic acids and/or carboxylic esters with hydrogen, which are characterized in that, in the non-reduced state, they comprise 20 to 80% by weight of CuO, 10 to 80% by weight of ZnO and 1 to 50% by weight of Al$_2$O$_3$ and are prepared by precipitating compounds of copper and of zinc onto aluminium oxide powder, and have such a pore size distribution that 5 to 15% of the total pore volume is in the pore diameter range of less than 150 Å and 80 to 95% of the total pore volume is in the pore diameter range of greater than 250 Å, which is determined by mercury intrusion (mercury pore symmetry) in a similar manner to DIN 66133 assuming a cylindrical pore model.

Preferred embodiments of the catalyst correspond to that which has already been detailed in the description of the process.

The catalysts according to the invention may be prepared, for example, as follows: aluminium oxide powder is suspended in water and heated to a temperature of 20 to 90° C., preferably 50 to 80° C. An aqueous solution having a copper salt, preferably copper nitrate, concentration of 0.1 to 3 mol/l, preferably 0.5 to 1.5 mol/l, and a corresponding amount of zinc salt, preferably zinc nitrate, are pumped from a feed vessel to the suspended aluminium oxide powder. The molar ratio of copper to zinc, calculated as metal, is 8:1 to 1:4, preferably 3.5:1 to 1:1.25 and more preferably 3.5:1 to 2.2:1. At the same time, an aqueous solution having a concentration of a base, preferably ammonium carbonate, sodium carbonate, sodium hydroxide or a mixture of these, of 0.1 to 5 mol/l, preferably 0.5 to 2 mol/l is added by pumping. The addition rates of the two solutions are adjusted in such a manner that the pH at the temperature at which the precipitation is carried out is maintained within the range from 5.9 to 9, preferably 5.9 to 8.1. The precipitation is carried out at a very constant temperature in the range from 20 to 90° C., preferably 50 to 80° C. After the precipitation, the resulting suspension is stirred at a temperature of 20 to 90° C., preferably 70 to 90° C. for a further period of 0.5 to 3 hours. The suspension is then filtered and the residue washed with water, preferably at 15 to 70° C., more preferably at 15 to 25° C. The filter cake is dried, for example, at temperatures of 70 to 150° C., optionally under reduced pressure. The drying may also be carried out simultaneously with a spray agglomeration, for example in a spray drier, to give particles having a substantially uniform diameter, preferably in the range from 10 to 80 µm. The dried material is then calcined at a temperature in the range from 300 to 900° C. over a period of 2 to 6 hours. When the catalyst is to be used in powder form, preference is given to calcining in the range from 400 to 800° C., and particular preference to calcining in the range from 450° C. to 700° C. When the material is to be agglomerated for use in a fixed bed reactor, for example by tableting or extruding, preference is given to calcining at 300 to 600° C. and particular preference to calcining at 300° C. to 500° C.

The calcined catalyst may be reduced by hydrogen, for example in the hydrogenation reactor in which the reaction according to the invention is effected. It is also possible to reduce the calcined catalyst in a separate reduction oven.

When the catalyst is to be used in a suspension reactor, the catalyst is advantageously used in the form of the powder.

For use in a fixed bed reactor, it is advantageous to subject the catalyst to a shaping, for example by tableting or extruding. To this end, assistants, for example graphite, magnesium stearate or zinc stearate may be added in an amount of 0.5 to 5% by weight. When shaping by tableting, preference is given to setting a lateral fracture hardness of 30 to 250 N, more preferably of 100 to 200 N, by adjusting the apparatus. The calcined powder may also be reduced before the shaping. After the shaping, there may be an additional calcination to further increase the mechanical stability and improve the chemical properties, for example at 400° C. to 900° C., preferably at 450° C. to 800° C. and more preferably at 450° C. to 700° C.

In a particular embodiment of the invention, a pore former may also be added to the powder before compacting, which results in an additional formation of pores by a subsequent calcination. Examples of useful pore formers include the uncalcined dried precipitation product of copper and zinc salts on aluminium oxide described here.

The invention is illustrated hereinbelow with the aid of examples. The examples represent individual embodiments of the invention, but the invention is not restricted to the examples.

EXAMPLES

Example 1 (Comparative)

Catalyst Preparation 72 g of aluminium oxide powder (specific surface area 146.5 m$^2$/g) is suspended in 4 l of water in a precipitating vessel and heated to 70° C. 15 kg of an aqueous solution comprising 2628 g of Cu(NO$_3$)$_2$.2.5H$_2$O and 1200 g of Zn(NO$_3$)$_2$.6H$_2$O are pumped from a feed vessel into the precipitation vessel within 3 hours. At the same time, an aqueous sodium carbonate solution of concentration 1 mol/l is added by pumping. The addition rate of the sodium carbonate solution is adjusted in such a manner that the pH is maintained within the range from 6.8 to 7. The precipitation is carried out at a temperature of 70° C. After the precipitation, the suspension is stirred at 70° C. for a further period of 2 hours. The suspension is then filtered and the residue is washed with water. The filter cake is dried at 120° C. under reduced pressure for 12 hours. The dried material is then calcined at 400° C. over a period of 4 hours. The calcination product is ground, mixed with 5% by weight of graphite and tableted using a tableting press to give cylinders having a height of 5 mm and a diameter of 5 mm. The lateral fracture hardness is set to 117 N. The specific surface area (BET) is 41.2 m$^2$/g and was determined according to DIN 66131. The lateral fracture hardness in the reduced state is 78 N. The total pore volume is 188.8 mM$^3$/g. The pore size distribution is such that 17.9% of the total pore volume is in the pore diameter range of less than 150 Å and 41.4% of the total pore volume is in the pore diameter range of greater than 250 Å. The exact pore size distribution is presented in Table 1.

Example 2

Catalyst Preparation

The catalyst from Example 1 as a finished oxidic tablet is calcined at 480° C. for a further 4 h. The lateral fracture hardness is 300 N. The specific surface area (BET) is 26.4 m$^2$/g. The lateral fracture hardness in the reduced state is 50 N. The total pore volume is 211.2 mm$^3$/g. The pore size distribution is such that 11.1% of the total pore volume is in the pore diameter range of less than 150 Å and 84.9% of the total pore volume is in the pore diameter range of greater than 250 Å. The exact pore size distribution is presented in Table 1.

Example 3

Catalyst Preparation

The preparation is similar to Example 1, except that the powder is calcined at 480° C. for 4 h before compacting. 5% of graphite is then added and the powder is tableted to give tablets having a diameter of 5 mm and a height of 3 mm. The lateral fracture hardness is 121 N. The specific surface area (BET) is 24.0 m$^2$/g. The lateral fracture hardness in the reduced state is 47 N. The total pore volume is 191.9 mm$^3$/g. The pore size distribution is such that 12.3% of the total pore volume is in the pore diameter range of less than 150 Å and 81.5% of the total pore volume is in the pore diameter range of greater than 250 Å. The exact pore size distribution is presented in Table 1.

Example 4 (Comparative)

Catalyst Preparation 72 g of aluminium oxide powder (specific surface area 146.5 m$^2$/g) is suspended in 4 l of water in a precipitating vessel and heated to 60° C. 15 kg of an aqueous solution comprising 2628 g of Cu(NO$_3$)$_2$.2.5H$_2$O and 1200 g of Zn(NO$_3$)$_2$.6H$_2$O are pumped from a feed vessel into the precipitation vessel within 3 hours. At the same time, an aqueous sodium carbonate solution of concentration 1 mol/l is added by pumping. The addition rate of the sodium carbonate solution is adjusted in such a manner that the pH is maintained within the range from 5.9 to 6.1. The precipitation is carried out at a temperature of 60° C. After the precipitation, the suspension is stirred at 60° C. for a further period of 2 hours. The suspension is then filtered and the residue is washed with water. The filter cake is dried at 120° C. under reduced pressure for 12 hours. The dried material is then calcined at 400° C. over a period of 4 hours. The calcination product is ground, mixed with 5% by weight of graphite and tableted using a tableting press to give cylinders having a height of 5 mm and a diameter of 5 mm. The lateral fracture hardness is set to 110 N. The specific surface area (BET) is 56.4 m$^2$/g. The lateral fracture hardness in the reduced state is 36 N. The total pore volume is 240.0 mm$^3$/g. The pore size distribution is such that 15.9% of the total pore volume is in the pore diameter range of less than 150 Å and 21.6% of the total pore volume is in the pore diameter range of greater than 250 Å. The exact pore size distribution is presented in Table 1.

Example 5 (Comparative)

Catalyst Preparation

The catalyst from Example 4 as a finished oxidic tablet is calcined at 700° C. for a further 4 h. The lateral fracture hardness is 350 N. The specific surface area (BET) is 7.0 m$^2$/g. The total pore volume is 112.0 mm$^3$/g. The pore size distribution is such that 17.2% of the total pore volume is in the pore diameter range of less than 150 Å and 79.2% of the total pore volume is greater than 250 Å. The exact pore size distribution is presented in Table 1.

Example 6 (Comparative)

Catalyst Preparation 61.5 g of aluminium oxide powder (specific surface area 146.5 m$^2$/g) is suspended in 4 l of water in a precipitating vessel and heated to 70° C. 12.8 kg of an aqueous solution comprising 2234 g of $Cu(NO_3)_2 \cdot 2.5H_2O$ and 896 g of $Zn(NO_3)_2 \cdot 6H_2O$ are pumped from a feed vessel into the precipitation vessel within 6 hours. At the same time, an aqueous sodium carbonate solution of concentration 1 mol/l is added by pumping. The addition rate of the sodium carbonate solution is adjusted in such a manner that the pH is maintained within the range from 7.9 to 8.1. The precipitation is carried out at a temperature of 70° C.

After the precipitation, the suspension is stirred at 70° C. for a further period of 2 hours. The suspension is then filtered and the residue is washed with water. The filter cake is dried at 120° C. under reduced pressure for 12 hours. The dried material is then calcined at 350° C. over a period of 4 hours. The calcination product is ground, mixed with 5% by weight of graphite and tabletted using a tableting press to give cylinders having a height of 5 mm and a diameter of 5 mm. The lateral fracture hardness is set to 176 N. The specific surface area (BET) is 57.3 $m^2/g$. The lateral fracture hardness in the reduced state is 34 N. The total pore volume is 165.8 $mm^3/g$. The pore size distribution is such that 53.8% of the total pore volume is in the pore diameter range of less than 150 Å and 26.8% of the total pore volume is in the pore diameter range of greater than 250 Å. The exact pore size distribution is presented in Table 1.

Example 7

Catalyst Preparation

The catalyst from Example 6 as a finished oxidic tablet is calcined at 600° C. for a further 4 h. The lateral fracture hardness is 158 N. The specific surface area (BET) is 15.4 $m^2/g$. The total pore volume is 214.4 $mm^3/g$. The pore size distribution is such that 10.2% of the total pore volume is in the pore diameter range of less than 150 Å and 88.9% of the total pore volume is in the pore diameter range of greater than 250 Å. The exact pore size distribution is presented in Table 1.

TABLE 1

| Pore diameter interval | Relative Hg pore volume [mm³/g] Catalyst from Example 1 | Relative Hg pore volume [%] Catalyst from Example 1 | Relative Hg pore volume [mm³/g] Catalyst from Example 2 | Relatives Hg pore volume [%] Catalyst from Example 2 | Relative Hg pore volume [mm³/g] Catalyst from Example 3 | Relative Hg pore volume [%] Catalyst from Example 3 | Relative Hg pore volume [mm³/g] Catalyst from Example 4 | Relative Hg pore volume [%] Catalyst from Example 4 |
|---|---|---|---|---|---|---|---|---|
| 2000000 Å–1000000 Å | 0 | 0 | 0 | 0 | 0.00 | 0.00 | 0 | 0 |
| 1000000 Å–500000 Å | 0.27 | 0.14 | 0.78 | 0.37 | 0.00 | 0.00 | 0.82 | 0.34 |
| 500000 Å–200000 Å | 0.41 | 0.21 | 0.49 | 0.23 | 0.38 | 0.20 | 0.47 | 0.19 |
| 200000 Å–100000 Å | 0.81 | 0.43 | 0.29 | 0.14 | 0.19 | 0.10 | 0.35 | 0.15 |
| 100000 Å–50000 Å | 1.22 | 0.64 | 0.39 | 0.18 | 0.38 | 0.20 | 0.58 | 0.24 |
| 50000 Å–20000 Å | 0.81 | 0.43 | 0.19 | 0.09 | 0.38 | 0.20 | 0.35 | 0.15 |
| 20000 Å–10000 Å | 0.00 | 0.00 | 0.10 | 0.05 | 0.00 | 0.00 | 0.12 | 0.05 |
| 10000 Å–5000 Å | 0.00 | 0.00 | 0.39 | 0.18 | 0.00 | 0.00 | 0.35 | 0.15 |
| 5000 Å–2000 Å | 0.00 | 0.00 | 4.18 | 1.98 | 0.76 | 0.39 | 0.82 | 0.34 |
| 2000 Å–1000 Å | 4.32 | 2.29 | 21.87 | 10.36 | 14.19 | 7.40 | 1.64 | 0.68 |
| 1000 Å–600 Å | 19.32 | 10.24 | 39.56 | 18.74 | 29.71 | 15.48 | 3.04 | 1.27 |
| 600 Å–400 Å | 18.38 | 9.74 | 52.98 | 25.09 | 54.68 | 28.50 | 6.20 | 2.58 |
| 400 Å–300 Å | 15.95 | 8.45 | 46.37 | 21.96 | 42.57 | 22.19 | 11.46 | 4.77 |
| 300 Å–250 Å | 16.62 | 8.80 | 11.57 | 5.48 | 13.06 | 6.80 | 25.72 | 10.72 |
| 250 Å–200 Å | 37.16 | 19.69 | 4.96 | 2.35 | 7.19 | 3.75 | 74.46 | 31.03 |
| 200 Å–150 Å | 39.73 | 21.05 | 3.60 | 1.70 | 4.73 | 2.47 | 75.51 | 31.47 |
| 150 Å–100 Å | 22.03 | 11.67 | 11.18 | 5.29 | 12.30 | 6.41 | 28.05 | 11.69 |
| 100 Å–50 Å | 10.27 | 5.44 | 11.08 | 5.25 | 9.27 | 4.83 | 8.65 | 3.60 |
| 50 Å–37 Å | 1.49 | 0.79 | 1.17 | 0.55 | 2.08 | 1.08 | 1.40 | 0.58 |
| Sum | 188.79 | 100 | 211.15 | 100 | 191.87 | 100 | 239.99 | 100 |

| Pore diameter interval | Relative Hg pore volume [mm³/g] Catalyst from Example 5 | Relative Hg pore volume [%] Catalyst from Example 5 | Relative Hg pore volume [mm³/g] Catalyst from Example 6 | Relative Hg pore volume [%] Catalyst from Example 6 | Relative Hg pore volume [mm³/g] Catalyst from Example 7 | Relative Hg pore volume [%] Catalyst from Example 7 |
|---|---|---|---|---|---|---|
| 2000000 Å–1000000 Å | 0.00 | 0.00 | 0 | 0 | 0 | 0 |
| 1000000 Å–500000 Å | 0.18 | 0.16 | 0.46 | 0.28 | 0.40 | 0.19 |
| 500000 Å–200000 Å | 0.00 | 0.00 | 0.58 | 0.35 | 0.40 | 0.19 |
| 200000 Å–100000 Å | 0.00 | 0.00 | 0.35 | 0.21 | 0.13 | 0.06 |
| 100000 Å–50000 Å | 0.45 | 0.40 | 0.00 | 0.00 | 0.13 | 0.06 |
| 50000 Å–20000 Å | 1.18 | 1.05 | 0.23 | 0.14 | 1.20 | 0.56 |
| 20000 Å–10000 Å | 1.09 | 0.97 | 0.12 | 0.07 | 7.71 | 3.60 |
| 10000 Å–5000 Å | 7.89 | 7.04 | 0.35 | 0.21 | 17.01 | 7.94 |
| 5000 Å–2000 Å | 25.02 | 22.35 | 1.27 | 0.76 | 24.72 | 11.53 |
| 2000 Å–1000 Å | 39.26 | 35.06 | 6.67 | 4.02 | 57.02 | 26.60 |

-continued

| Pore diameter interval | Relative Hg pore volume [mm³/g] Catalyst from Example 5 | Relative Hg pore volume [%] Catalyst from Example 5 | Relative Hg pore volume [mm³/g] Catalyst from Example 6 | Relative Hg pore volume [%] Catalyst from Example 6 | Relative Hg pore volume [mm³/g] Catalyst from Example 7 | Relative Hg pore volume [%] Catalyst from Example 7 |
|---|---|---|---|---|---|---|
| 1000 Å–600 Å | 10.52 | 9.39 | 11.27 | 6.80 | 46.52 | 21.70 |
| 600 Å–400 Å | 1.54 | 1.38 | 10.24 | 6.18 | 24.99 | 11.66 |
| 400 Å–300 Å | 0.82 | 0.73 | 7.71 | 4.65 | 8.77 | 4.09 |
| 300 Å–250 Å | 0.73 | 0.65 | 5.18 | 3.12 | 1.59 | 0.74 |
| 250 Å–200 Å | 1.18 | 1.05 | 8.17 | 4.93 | 0.93 | 0.43 |
| 200 Å–150 Å | 2.90 | 2.59 | 24.05 | 14.50 | 1.06 | 0.50 |
| 150 Å–100 Å | 10.97 | 9.80 | 57.52 | 34.70 | 6.51 | 3.04 |
| 100 Å–50 Å | 7.80 | 6.96 | 31.64 | 19.08 | 15.28 | 7.13 |
| 50 Å–37 Å | 0.45 | 0.40 | 0.00 | 0.00 | 0.00 | 0.00 |
| Sum | 111.98 | 100 | 165.81 | 100 | 214.37 | 100 |

Examples 8 to 14

Catalyst Application

A vertical, heat-insulated, high pressure tube made of non-rusting, acid-resistant material of diameter 45 mm and length 1 m which has been purged in advance with nitrogen to free it of oxygen is charged with 1.4 l of the catalysts from Examples 1 to 7. To activate the catalyst, a nitrogen stream (5 m³/h, STP) is initially passed through the catalyst bed at 200° C. for 6 hours. The catalyst is then reduced by gradually admixing in hydrogen at a temperature between 180 and 200° C. at a nitrogen pressure of 200 bar, and the starting content may not exceed 10 to 15% by volume. Over the period of 24 hours, the proportion of nitrogen is decreased more and more until finally pure hydrogen flows through the reactor. The reaction is complete when no more water of reaction is formed.

After the activation of the catalyst, the hydrogen pressure is increased to 300 bar and a volume stream of 5 m³/h (STP) is set. Hexanediol 1,6-adipate which has been obtained by esterifying adipic acid with 1,6-hexanediol in a ratio of 1:1.1 (cf. EP-A 0 721 928) is then conveyed through the reactor. The feed amount and the corresponding temperature can be taken from Table 2 which follows. Each of the pairs of feed amount and temperature values quoted in Table 2 is maintained for at least 48 h. The reaction mixture leaving the reaction tube is cooled in a second heat exchanger (water cooler) to less than 60° C. at 300 bar of hydrogen pressure and separated in a gas separator from excess hydrogen which is recycled into the hydrogenation system. After further cooling to a temperature of less than 30° C. and decompression to atmospheric pressure, the reaction product is investigated by gas chromatography. The crude yield of 1,6-hexanediol is likewise quoted in Table 2.

TABLE 2

| Example | Catalyst | Feed amount of ester | Temperature | Crude yield of 1,6-hexanediol |
|---|---|---|---|---|
| Example 8 | from Example 1 | 200 ml/h | 240° C. | 96.7% |
| | | 400 ml/h | 240° C. | 84.6% |
| | | 600 ml/h | 240° C. | 77.7% |
| | | 600 ml/h | 260° C. | 80.6% |
| | | 400 ml/h | 260° C. | 81.7% |

The experiment was completed after a total running time of 2080 h. At this time, the activity of the catalyst was still virtually unchanged.

TABLE 2-continued

| Example | Catalyst | Feed amount of ester | Temperature | Crude yield of 1,6-hexanediol |
|---|---|---|---|---|
| Example 9 | from Example 2 | 200 ml/h | 240° C. | 94.9% |
| | | 400 ml/h | 240° C. | 94.0% |
| | | 600 ml/h | 240° C. | 89.2% |
| | | 600 ml/h | 260° C. | 87.4% |
| | | 400 ml/h | 260° C. | 92.4% |

The experiment was completed after a total running time of 900 h. At this time, the activity of the catalyst was still virtually unchanged.

| Example 10 | from Example 3 | 200 ml/h | 240° C. | 97.3% |
|---|---|---|---|---|
| | | 400 ml/h | 240° C. | 97.5% |
| | | 600 ml/h | 240° C. | 96.6% |
| | | 600 ml/h | 260° C. | 93.0% |
| | | 400 ml/h | 260° C. | 91.9% |
| | | 900 ml/h | 260° C. | 93.4% |
| | | 1000 ml/h | 260° C. | 91.7% |

The experiment was completed after a total running time of 3412 h. At this time, the activity of the catalyst was still virtually unchanged.

| Example 11 | from Example 4 | 200 ml/h | 240° C. | 96.2% |
|---|---|---|---|---|
| | | 400 ml/h | 240° C. | 80.5% |
| | | 600 ml/h | 240° C. | 73.1% |
| | | 600 ml/h | 260° C. | 74.7% |
| | | 400 ml/h | 260° C. | 85.0% |

The experiment was completed after a total running time of 526 h. At this time, the activity of the catalyst was still virtually unchanged.

| Example 12 | from Example 5 | 200 ml/h | 240° C. | 90.6% |
|---|---|---|---|---|
| | | 400 ml/h | 240° C. | 93.0% |
| | | 600 ml/h | 240° C. | 83.6% |
| | | 600 ml/h | 260° C. | 86.3% |
| | | 400 ml/h | 260° C. | 91.3% |

The experiment was completed after a total running time of 862 h. At this time, the activity of the catalyst was still virtually unchanged.

| Example 13 | from Example 6 | 200 ml/h | 240° C. | 97.5% |
|---|---|---|---|---|
| | | 400 ml/h | 240° C. | 89.2% |
| | | 600 ml/h | 240° C. | 85.3% |
| | | 600 ml/h | 260° C. | 85.4% |
| | | 400 ml/h | 260° C. | 88.3% |

The experiment was completed after a total running time of 520 h. At this time, the activity of the catalyst was still virtually unchanged.

| Example 14 | from Example 7 | 200 ml/h | 240° C. | 97.9% |
|---|---|---|---|---|
| | | 400 ml/h | 240° C. | 97.3% |
| | | 600 ml/h | 240° C. | 96.5% |
| | | 600 ml/h | 260° C. | 96.1% |
| | | 800 ml/h | 240° C. | 93.7% |
| | | 800 ml/h | 250° C. | 95.8% |
| | | 1000 ml/h | 260° C. | 94.7% |
| | | 1100 ml/h | 260° C. | 93.1% |

The experiment was completed after a total running time of 642 h. At this time, the activity of the catalyst was still virtually unchanged.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A process for preparing alcohols comprising reacting carboxylic acids and/or carboxylic esters with hydrogen in the presence of a catalyst;
wherein the catalyst is in a non-reduced state and comprises 20 to 80% by weight of CuO, 10 to 80% by weight of ZnO and 1 to 50% by weight of $Al_2O_3$, and has a pore size distribution in which 5 to 15% of the total pore volume is in the pore diameter range of less than 150 Å and 80 to 95% of the total pore volume is in the pore diameter range of greater than 250 Å.

2. The process according to claim 1, wherein the reaction is carried out in the presence of a catalyst which is prepared by precipitating compounds of zinc and copper onto aluminum oxide powder.

3. The process according to claim 1, wherein the reaction is carried out at a temperature of 100 to 350° C.

4. The process according to claim 1, wherein the reaction is carried out at a pressure of 50 to 400 bar.

5. The process according to claim 1, wherein the reaction is carried out in a suspension reactor.

6. The process according to claim 1, wherein the catalyst is present as a powder having a particle size ranging from 20 to 100 μm.

7. The process according to claim 1, wherein the reaction is carded out in a fixed bed reactor.

8. The process according to claim 1, wherein a carboxylic acid is used and the reaction of the carboxylic acid with hydrogen is carried out in an alcohol.

9. The process according to claim 1, wherein a carboxylic ester mixture made from adipic acid and hexanediol is used.

10. The process according to claim 1, wherein the catalyst is prepared using aluminum oxide powder having a particle size ranging from 1 to 100 μm.

11. The process according to claim 1, wherein the catalyst is prepared using aluminum oxide powder having a specific surface area ranging from 100 to 400 $m^2/g$.

12. A catalyst for the preparation of alcohols, wherein said alcohols are prepared by reacting carboxylic acids and/or carboxylic esters with hydrogen and wherein the catalyst is in a non-reduced state and comprises 20 to 80% by weight of CuO, 10 to 80% by weight of ZnO and 1 to 50% by weight of $Al_2O_3$, and has a pore size distribution in which 5 to 15% of the total pore volume is in the pore diameter range of less than 150 Å and 80 to 95% is in the pore diameter range of greater than 250 Å.

13. The catalyst according to claim 12, which is prepared by precipitating compounds of zinc and copper onto aluminum oxide powder.

14. The catalyst according to claim 12, wherein the catalyst has a total pore volume of 100 to 350 $mm^3/g$.

15. The catalyst according to claim 12, which has a BET surface area of 5 to 150 $m^2/g$.

16. The catalyst according to claim 12, wherein the catalyst is in the form of a tablet.

17. The catalyst according to claim 12, which is prepared by precipitating copper and zinc from their salts onto aluminum oxide powder, filtering and washing the product, then drying the product at a temperature ranging from 70 to 150° C., calcining the product at a temperature ranging from 300° C. to 600° C. and then tableting the product and optionally further calcining the tablets obtained at a temperature ranging from 400° C. to 900° C.

18. The catalyst according to claim 12, wherein the catalyst is prepared by precipitating copper and zinc from their salts onto aluminum oxide powder, filtering and washing the product, drying the product at a temperature ranging from 70° C. to 150° C., tableting the product and subjecting the product to calcining at a temperature ranging from 300° C. to 900° C.

* * * * *